United States Patent [19]

Liberman

[11] Patent Number: 5,001,047
[45] Date of Patent: Mar. 19, 1991

[54] METHOD OF PRESERVING ORGANS

[75] Inventor: Barnet L. Liberman, 421 Hudson St., New York, N.Y. 10014

[73] Assignee: Barnet L. Liberman, New York, N.Y.

[21] Appl. No.: 219,340

[22] Filed: Jul. 14, 1988

[51] Int. Cl.$^5$ ................................................ A01N 1/02
[52] U.S. Cl. ............................................ 435/1; 435/2; 62/64; 62/78
[58] Field of Search ................ 435/1; 426/524; 62/64, 62/78; 252/70, 71, 76; 128/DIG. 3, DIG. 27

[56] References Cited

U.S. PATENT DOCUMENTS 4,559,298  12/1985  Fahy ........................................ 435/1
4,840,034   6/1989  Liberman ................................. 435/1

Primary Examiner—Sam Rosen
Attorney, Agent, or Firm—Cohen, Pontani & Lieberman

[57] ABSTRACT

A method of preserving harvested viable organs for transplant is provided. The method includes the steps of preparing a brine including a cruciferous oil and a glycol, cooling the brine, and subjecting the harvested viable organ to the cooled brine in order to chill the viable organ and maintain its viability.

19 Claims, No Drawings

METHOD OF PRESERVING ORGANS

BACKGROUND OF THE INVENTION

This invention relates generally to methods of preserving organs and, in particular, to a method of preserving viable organs of a mammalian subject which prevents deterioration of the cellular structure of the organ.

Transplant of viable organs from the body of one human being to another human being is almost becoming a commonplace occurrence. One of the difficult aspects of these procedures is maintenance of the viability of these organs during the time after removal from a donor until transplantation into a recipient. Chilling of harvested organs to maintain viability is common. In chilling the organs, it is important to minimize deterioration in the cellular structure.

U.S. Pat. No. 4,601,909 issued to Nagoshi on July 22, 1986, discloses a Method of Freezing Fishery Products. The method includes the steps of preparing a brine containing rapeseed oil, propylene glycol, calcium chloride and water, cooling the brine and immersing the seafood in the cooled brine until it is frozen. Such a brine prevents or reduces the breakdown of muscle tissue in the seafood due to ice crystal formation. The resultant deterioration in quality from freezing is thus prevented.

A similar process for Quick Freezing of Meat is disclosed and claimed in U.S. Pat. No. 4,654,217 issued to the same inventor on Mar. 31, 1987. The process disclosed in this later patent is similar to that disclosed in the earlier patent except that it is applicable to beef, poultry, pork and the like.

U.S. Pat. No. 4,657,768 issued to Nagoshi on Apr. 14, 1987, discloses a Freezing Method for Perishable Foods which includes placing a perishable food in a heat conducting container and causing the other surface of the heat conducting container to contact cooled brine o a liquified gas. Accordingly, the perishable food is frozen quickly without immersion.

U.S. Pat. No. 4,689,963 issued to Sakai on Sept. 1, 1987, relates to a Method of Freezing Foods. The method of Sakai is similar to the method of Nagoshi except that a layer of brine is placed in the heat conducting container along with the perishable food.

There is no teaching or suggestion in any of these patents that these processes can be used to preserve harvested viable organs for transplant.

Accordingly, it is desirable to provide a process for maintaining the viability of harvested organs.

It is, therefore, an object of the invention to provide a process for chilling harvested viable organs.

Another object of the invention is to provide a method of chilling harvested viable organs using a brine including an effective amount of a suitable oil.

A further object of the invention is to provide a method of chilling harvested viable organs which does not destroy the cellular structure of the organs.

Still another object of the invention is to provide an economical method of chilling harvested viable organs.

Still other objects and advantages of the invention will be apparent from the specification.

SUMMARY OF THE INVENTION

Generally speaking, in accordance with the invention, a method for preserving viable organs of a mammalian subject for transplant is provided. The method includes the steps of preparing a brine including a cruciferous oil; cooling the brine to a temperature between about $-22°$ and $-43.6°$ F.; harvesting a viable organ for transplant; and subjecting the harvested viable organ to the cooled brine for a period of time sufficient to chill the organ and maintain the viability of the organ. The brine generally includes a glycol, a salt and water in addition to the cruciferous oil.

The invention accordingly comprises the several steps and the relation of one or more of such steps with respect to each of the others thereof which will be exemplified in the method hereinafter disclosed and the scope of the invention will be indicated in the claims.

DETAILED DESCRIPTION OF THE PREFERRED EMBODIMENTS

The first step of the process of chilling harvested viable organs in accordance with the invention is preparation of a suitable brine solution. The brine solution includes a cruciferous oil. In a preferred embodiment, oil from a plant of the genus Brassica is used. These oils include, but are not limited to, oil of Brassica campestris, otherwise known as rapeseed oil, and oil of Brassica hirta, also known as mustard oil.

Rapeseed oil has a solidification point of 14° F. ($-10°$ C.), a specific gravity at 59° F. (15° C.) of 0.915, a refractive index at 122° F. (50° C.) of 1.4706, an iodine value of 98.6 and a saponification value of 174.7. The oil includes about 1% palmitic acid, the only saturated component of the oil, about 32% oleic acid, about 15% linoleic acid, about 1% linolenic acid and about 50% erucic acid. Palmitic acid, otherwise known as hexadecanoic acid is a saturated fatty acid having 16 carbon atoms and a molecular weight of 256.4.

Oleic acid, also known as (Z)-9-octadecenoic acid, has 18 carbon atoms and a molecular weight of 282.5. The position of unsaturation is between the ninth and tenth carbon atoms in the chain. The molecule has a cis configuration.

Linoleic acid has two positions of unsaturation and is also known as cis,cis-9,12-octadecadienoic acid. The acid has 18 carbon atoms and a molecular weight of 280.5.

Linolenic acid has three positions of unsaturation and is also known as (Z,Z,Z)-9,12,15-octadecatrienoic acid. Linolenic acid has 18 carbon atoms and a molecular weight of 278.4.

Erucic acid, a major component of the oils of the genus Brassica, is also known as (Z)-13-docosenoic acid. Erucic acid has 22 carbon atoms with one position of unsaturation and a molecular weight of 338.6.

Mustard oil is similar. Mustard oil has a specific gravity at 59° F. of 0.9145, a refractive index at 122° F. of 1.475, an iodine value of 102 and a saponification value of 174. Mustard oil includes 1.3% by weight myristic acid, the only saturated acid, 27.2% by weight oleic acid, 16.6% by weight linoleic acid, 1.8% by weight linolenic acid, 1.1% by weight behenic acid, 1.0% by weight lignoceric acid and 51.0% by weight erucic acid. Myristic acid, also known as tetradecanoic acid, has 14 carbon atoms and a molecular weight of 228.4.

Behenic acid is also known as docosanoic acid. It has 22 carbon atoms and a molecular weight of 340.6. Lignoceric acid, also known as tetracosanoic acid, has 24 carbon atoms and a molecular weight of 368.6. The other components of mustard oil are described above.

The oil is used in an amount less than about 1% by weight, more preferably less than about 0.8% by weight and most preferably between about 0.1 and 0.5% by weight of the brine.

It is to be understood that oils other than rapeseed oil and mustard oil can be used in accordance with the invention. For example, synthetic oils having the characteristics described would be useful. In addition, the manner in which the oils function is described in detail below and it will be readily apparent that other oils will function acceptably in accordance with the invention and can be readily determined.

In addition to the cruciferous oil, the brine also generally includes a glycol, an inorganic salt and water. Suitable glycols include, but are not limited to, ethylene glycol, propylene glycol, benzylene glycol, butylene glycol, diethylene glycol, diphenyl glycol, ethylidene glycol, and the like. Any glycol can be used alone or in combination with other glycols. Propylene glycol is used in a preferred embodiment. The glycol component is present in an amount between about 30 and 50% by weight of the brine, more preferably between about 35 and 45% by weight and most preferably in an amount of about 40% by weight.

Salts which are useful in accordance with the invention include, but are not limited to, calcium chloride, calcium bromide, calcium iodide, potassium chloride, potassium bromide, potassium iodide and the like. In a preferred embodiment, calcium chloride is used. The salt is present in an amount between about 5 and 15% by weight of the brine, more preferably in an amount between about 7 and 13% by weight and most preferably in an amount of about 10% by weight.

Water is present in an amount between about 40 and 60% by weight, more preferably in an amount between about 45 and 55% by weight and most preferably in an amount of about 50% by weight.

In an especially preferred embodiment, the brine includes between about 0.1 and 0.5% by weight cruciferous oil, about 40% by weight propylene glycol, about 10% by weight calcium chloride and a balance of water. The cruciferous oil is preferably rapeseed oil.

It is presently believed that when the brine including the oil is cooled to a temperature between about $-22°$ and $-43.6°$ F., fine ice crystals form in the brine and are uniformly distributed. These crystals permit efficient cold transfer and an increase in the expected chilling rate of a harvested organ immersed in the brine. Consequently, the time required to chill the harvested organ is reduced. In a preferred embodiment, means are provided for withdrawing heat from the brine as a harvested organ is brought into a heat transfer relationship therewith. This permits the temperature of the brine to be maintained substantially constant when a harvested organ at a nominal body temperature of 98.6° F. is introduced. Accordingly, the harvested organ can be chilled rapidly with minimum formation of ice crystals, breakdown of cellular tissue and deterioration of the sample.

Viable organs are harvested by known techniques. The organs are then chilled by placement in a heat transfer relationship with the cooled brine and viability can be maintained until the organ is transplanted. The organ is generally sufficiently chilled after immersion for less than about 2 minutes, more preferably between about ½ and 1½ minutes. The process is particularly useful because damage to the cellular structure of the organs is minimized and viability is maintained.

In an alternate method, which is useful in accordance with the invention, the organ can be chilled or frozen by placement in a heat-conducting pan or tray. The opposite side of the pan or tray is then placed in contact with the cooled brine described. In a further alternate embodiment, brine is placed in the heat-conducting pan or tray along with the harvested organ and the opposite side of the tray is placed into contact with the cooled brine in order to chill or freeze the organ.

The process is useful for maintaining viability of harvested viable organs until a suitable recipient can be notified and prepared. The organs with which the process is useful include liver, heart, eyes and the like and the process is not intended to be limited by the organs with which it is used. In fact, the process is also useful for maintaining the viability of severed limbs prior to reattachment and muscle tissue prior to transplant. It is to be understood for purposes of this invention that the terms "organs" and "harvested organs" also include severed limbs, muscle tissue and the like.

It will thus be seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients of compounds recited in the single are intended to include compatible mixtures of such ingredients wherever the sense permits.

What is claimed is:

1. A method of preserving harvested viable organs of a mammalian subject for transplant comprising:
   preparing a brine comprising at least 0.1% by weight of cruciferous oil, between about 30 and 50% by weight of glycol, and between about 5 and 15% by weight of an inorganic salt, the balance being water;
   cooling the brine to a temperature between about $-22°$ and $-43.6°$ F.; and
   subjecting the harvested viable organ to a heat transfer relationship with the cooled brine in order to chill said organ and maintain its viability until it is transplanted.

2. The method of preserving harvested viable organs of claim 1, wherein the oil is extracted from a plant of the genus Brassica.

3. The method of preserving harvested viable organs of claim 1, wherein the oil is selected from the group consisting of rapeseed oil, mustard oil, and mixtures thereof.

4. The method of preserving harvested viable organs of claim 1, wherein the oil contains erucic acid as the single largest component.

5. The method of preserving harvested viable organs of claim 1, wherein the oil contains less than about 2% saturated components.

6. The method of preserving harvested viable organs of claim 1, wherein the oil is used in an amount between about 0.1 and 0.5% by weight of the brine.

7. The method of preserving harvested viable organs of claim 1, wherein the glycol is propylene glycol.

8. The method of preserving harvested viable organs of claim 1, wherein the glycol is present in an amount between about 35 and 40% by weight of the brine.

9. The method of preserving harvested viable organs of claim 1, wherein the salt is calcium chloride.

10. The method of preserving harvested viable organs of claim 1, wherein the salt is present in an amount between about 7 and 13% by weight of the brine.

11. The method of preserving harvested viable organs of claim 1, wherein the water is present in an amount between about 4 and 55% by weight of the brine.

12. The method of preserving harvested viable organs of claim 1, wherein the organ is subjected to a heat transfer relationship with the chilled brine by immersing the organ in the brine.

13. The method of preserving harvested viable organs of claim 1, wherein the organ is subjected to a heat transfer relationship with the cooled brine by placing the organ in a heat transfer tray and bringing the opposite side of the heat transfer tray into contact with the cooled brine.

14. The method of preserving harvested viable organs of claim 1, wherein the organ is subjected to a heat transfer relationship with the cooled brine by placing the organ and a small amount of brine into a heat transfer tray and bringing the opposite side of the heat transfer tray into contact with the cooled brine.

15. The method of preserving harvested viable organs of claim 14, wherein the heat transfer tray has a bottom and the small amount of brine at least covers the bottom of the heat transfer tray.

16. A method of preserving harvested viable organs of a mammalian subject for transplant, comprising:
preparing a brine comprising an effective amount of a suitable oil for increasing the chilling rate of the organ brought into a heat transfer relationship therewith so as to minimize deterioration in the cellular structure of the organ, between about 30 and 50% by weight of a glycol, and between about 5 and 15% by weight of an inorganic salt, the balance being water;
cooling the brine to a temperature between about $-22°$ and $-43.6°$ F.; and
subjecting the harvested viable organ to a heat transfer relationship with cooled brine in order to chill the organ and maintain its viability until it is transplanted.

17. The method of preserving harvested viable organs of claim 16, wherein the brine includes between about 0.1 and 1% by weight of a cruciferous oil.

18. The method of preserving harvested viable organs of claim 17, wherein the oil is rapeseed oil.

19. The method of preserving harvested viable organs of claim 16, wherein the brine includes between about 0.1 and 0.5% by weight of a cruciferous oil, between about 35 and 45% by weight of a glycol, between 7 and 13% by weight of an inorganic salt and a balance of water.

* * * * *